US005423853A

United States Patent [19]

Lasvignes

[11] Patent Number: 5,423,853

[45] Date of Patent: Jun. 13, 1995

[54] PAIN RELIEF CLIP FOR AN EAR

[76] Inventor: Carlos M. Lasvignes, Martin De Los Heros, 57, 28008 Madrid Spain

[21] Appl. No.: 123,969

[22] Filed: Sep. 21, 1993

[30] Foreign Application Priority Data

Sep. 22, 1992 [ES] Spain .................................. 9202773

[51] Int. Cl.[6] .............................................. A61B 17/00

[52] U.S. Cl. .................................... 606/204; 606/151; 606/201

[58] Field of Search ............... 606/151, 157, 158, 201, 606/207, 204, 204.15, 204.35, 204.45, 204.55; 227/902; 24/562, 561, 545, 543

[56] References Cited

U.S. PATENT DOCUMENTS

| | | | |
|---|---|---|---|
| D. 191,108 | 8/1961 | Dahlen | 24/562 |
| 2,070,939 | 2/1937 | Whitney | 24/562 |
| 2,396,389 | 3/1946 | Reynolds | 24/562 |
| 2,574,144 | 11/1951 | Engstrom | 24/562 |
| 4,319,574 | 3/1982 | Sun et al. | 606/204 |
| 4,514,885 | 5/1985 | Delahousse et al. | 24/562 |
| 4,616,113 | 10/1986 | Jank et al. | 24/562 |
| 4,686,983 | 8/1987 | Leisman et al. | 606/151 |

FOREIGN PATENT DOCUMENTS

| | | | |
|---|---|---|---|
| 2626772 | 8/1989 | France | 606/151 |
| 8301618 | 12/1984 | Netherlands | 606/151 |

*Primary Examiner*—Stephen C. Pellegrino

*Assistant Examiner*—Jeffrey A. Schmidt

*Attorney, Agent, or Firm*—Keck, Mahin & Cate

[57] ABSTRACT

A clip to be attached to an ear for alleviating pain includes a first plate having a rough inner surface for placing on a front portion of the ear, a second plate having a smooth inner surface for placing on a rear portion of the ear and an elongated spring connector having one end attached to the first plate and the other end attached to the second plate. The rough inner surface of the first plate has bumps substantially covering the surface. The first and second plates may have differently shaped peripheral contours from each other, and the outer surface of each plate is smooth. The elongated spring connector includes a pair of curved arm portions and a U-shaped portion therebetween, and the arm portions cross each other distally from the U-shaped portion. The spring connector includes a pair of tab portions spaced opposite to each other for pressing together against the force of the spring to open the clip and for releasing to close the clip. The first and second plates are disposed on ends of the arm portions with inner surfaces facing each other and are separated from each other by pressing the tab portions toward each other. In open position the inner surfaces of the first and second plates are spaced away from each other and in closed position the inner surfaces of the first and second plates lie against each other. The spring connector normally urges the clip into closed position.

5 Claims, 1 Drawing Sheet

PAIN RELIEF CLIP FOR AN EAR

FIELD OF THE INVENTION

The invention relates to a clip for attaching to the ear for aural acupuncture.

SUMMARY OF THE INVENTION

The invention is a clip for placing on the ear to treat general pain and other symptoms such as nervous states, allergies, tingling sensation in the arms or hands, etc., and symptoms of other illnesses. The properties of this device are derived from the therapeutic technique known as aural acupuncture. One or more of these devices may be placed on one or both ears, positioned according to the symptoms caused by the illnesses to be treated.

A clip to be attached to an ear for alleviating pain includes a first plate having a rough inner surface for placing on a front portion of the ear, a second plate having a smooth inner surface for placing on a rear portion of the ear and an elongated spring connector having one end attached to the first plate and the other end attached to the second plate. The rough inner surface of the first plate has bumps substantially covering the surface. The first and second plates may have differently shaped peripheral contours from each other, and the outer surface of each plate is smooth. The elongated spring connector includes a pair of curved arm portions and a U-shaped portion therebetween, and the arm portions cross each other distally from the U-shaped portion. The spring connector includes a pair of tab portions spaced opposite to each other for pressing together against the force of the spring to open the clip and for releasing to close the clip. The first and second plates are disposed on ends of the arm portions with inner surfaces facing each other and are separated from each other by pressing the tab portions toward each other. In open position the inner surfaces of the first and second plates are spaced away from each other and in closed position the inner surfaces of the first and second plates lie against each other. The spring connector normally urges the clip into closed position.

DETAILED DESCRIPTION OF THE PREFERRED EMBODIMENTS

Figure 1:
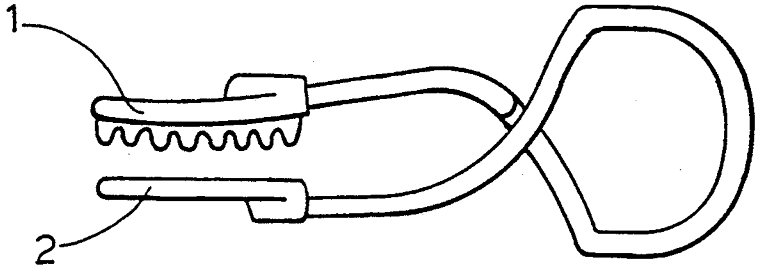
FIG. 1 is a side elevational view of a clip according to the invention.
Figure 2:
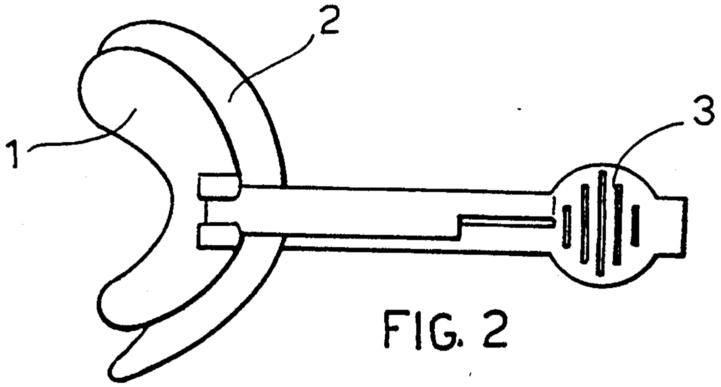
FIG. 2 is a top view of the device of FIG. 1.
Figure 3:
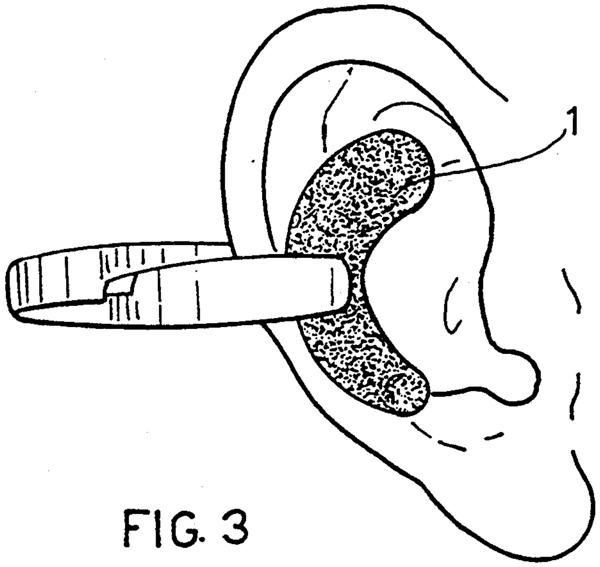
FIG. 3 is a schematic view showing a device positioned in an ear.

An aural clip, as illustrated in FIGS. 1 and 2, may, when placed on the ear, as illustrated in FIG. 3, be used to treat various pathological symptoms.

A clip for use in an ear, illustrated in FIGS. 1 to 3, has small plates 1 and 2 attached to each end thereof. The plates are differently shaped according to the part of the ear to which each plate is to be clipped. End plate 1 is smooth on the outer surface and rough with small bumps on the inner surface. End plate 2 is smooth on both the inner and outer surfaces. When not in use, the clip remains closed with the inner surface of end plate 1 in contact with the inner surface of end plate 2, due to the spring-action of the clip. The clip is opened by pressing the two opposing tabs 3 on the body of the clip between the thumb and forefinger.

In order to place the device on the patient's ear, the clip is opened by pressing the two tabs 3 towards each other. Once in place, the tabs 3 are released, leaving the device clipped to the ear by pressure between the inner surface of plate 1 and the inner surface of plate 2. The pressure on the ear from the inner surface of end 1, which is rough, provides the therapeutic effect.

The clips are differently configured, according to whether they are to be applied to the top, lower middle or inside of the ear, or to the left or right ear. The perimeter shape of plates 1 and 2 is determined according to the position on the ear in which the clip is to be used.

The shape of plates 1 and 2 are similar to the shape of the ear to which they are to be clipped. Thus, different types of clips can be distinguished, each with a different shape, depending on whether they are to be clipped to the top, lower middle or inside of the ear. These, in turn, can be divided into two types, depending on whether the clip is meant for the right or left ear. FIGS. 1 to 3 show examples of typical clips. FIG. 3 shows an example of a clip designed to be used on the lower part of the right ear. When clipped onto the ear, the rough inner surface of plate 1 is placed on the back of the ear, and the smooth inner surface of plate 2 is placed on the front of the ear, normally relieving the symptoms. The plates 1 and 2 are generally shaped asymmetrically which indicates whether they are intended for use on the left ear or the right ear.

While the invention has been described above with respect to certain embodiments thereof, variations and modifications may be made without departing from the spirit and scope of the invention.

What is claimed is:

1. A device for alleviating pain comprising a clip for attaching to an ear, said clip comprising:
   - a first plate having a rough inner surface for placing on a front portion of the ear;
   - a second plate having a smooth inner surface for placing on a rear portion of the ear;
   - an elongated spring connector supporting said first plate at a first end of said spring connector and said second plate at a second end of said spring connector, wherein said spring connector comprises a pair of tab portions spaced from each other in opposed positions on said connector for pressing together against the force of said spring to open said clip and for releasing to close said clip, wherein in open position said inner surfaces of said first and second plates are spaced away from each other and in closed position said inner surfaces of said first and second plates lie against each other, said spring connector normally urging said clip into closed position, wherein outer surfaces of said first and second plates are smooth.

2. A device according to claim 1 wherein said rough inner surface of said first plate comprises a plurality of bumps.

3. A device according to claim 2 wherein the plurality of bumps substantially cover said rough inner surface.

4. A device according to claim 1 wherein each of said first and second plates has a differently shaped peripheral contour from the other.

5. A device according to claim 1 wherein said elongated spring connector comprises a pair of arm portions and a U-shaped portion between said arm portions, a pair of substantially planar tab portions disposed one on each arm portion, facing each other adjacent said U-shaped portion, said first and second plates being disposed on ends of said arm portions with inner surfaces thereof facing each other wherein said arm portions are curved and cross each other between the tab portions and the first and second plates.

* * * * *